(12) United States Patent
Eckert et al.

(10) Patent No.: US 9,194,776 B2
(45) Date of Patent: Nov. 24, 2015

(54) PROCESSOR FOR WORKING ON HISTOLOGICAL SAMPLES

(71) Applicant: Leica Biosystems Nussloch GmbH, Nussloch (DE)

(72) Inventors: Ralf Eckert, Schriesheim (DE); Hermann Ulbrich, Bad Schonborn (DE); Stella Knorr, Brighton (AU); Graeme Robertson, Ferntree Gully (AU)

(73) Assignee: Leica Biosystems Nussloch GmbH, Nussloch (DE)

( * ) Notice: Subject to any disclaimer, the term of this patent is extended or adjusted under 35 U.S.C. 154(b) by 25 days.

(21) Appl. No.: 14/204,633

(22) Filed: Mar. 11, 2014

(65) Prior Publication Data
US 2014/0273085 A1  Sep. 18, 2014

(30) Foreign Application Priority Data

Mar. 15, 2013  (DE) .................. 10 2013 204 647

(51) Int. Cl.
*A61B 10/00* (2006.01)
*G01N 1/31* (2006.01)
*G01N 1/36* (2006.01)

(52) U.S. Cl.
CPC ... *G01N 1/31* (2013.01); *G01N 1/36* (2013.01)

(58) Field of Classification Search
CPC ....................................... G01N 1/30
See application file for complete search history.

(56) References Cited

U.S. PATENT DOCUMENTS

| 2002/0131896 | A1 | 9/2002 | Hunnell et al. |
| 2004/0091395 | A1 | 5/2004 | Ward et al. |
| 2007/0243626 | A1 | 10/2007 | Windeyer et al. |
| 2008/0113440 | A1 | 5/2008 | Gurney et al. |
| 2010/0086964 | A1* | 4/2010 | Walter et al. ............ 435/40.52 |
| 2012/0052526 | A1 | 3/2012 | Ulbrich et al. |

FOREIGN PATENT DOCUMENTS

| DE | 102007022014 A1 | 11/2008 |
| DE | 102007044116 A1 | 4/2009 |
| JP | H3-68866 A | 3/1991 |

* cited by examiner

*Primary Examiner* — Jyoti Nagpaul
(74) *Attorney, Agent, or Firm* — Sughrue Mion, PLLC

(57) ABSTRACT

The invention relates to a processor for working on histological samples. The processor has an inlet for the insertion of a fixing container, particularly a closed fixing container, with the samples located in the latter.

13 Claims, 7 Drawing Sheets

PROCESSOR FOR WORKING ON HISTOLOGICAL SAMPLES

The invention relates to a processor for working on histological samples, an automated system for working on histological samples, a holding arrangement and a method for working on histological samples.

The aim of treating a histological sample, taken from a patient for example, is to bring the sample to a state in which it can be cut into thin sections with a microtome. This treatment takes place in a plurality of work stations. The ability of the sample to be cut can be achieved, for example, by a process in which a medium that mechanically stabilizes the tissue is introduced (by infiltration) into the tissue in a plurality of successive work steps. Alternatively, the tissue can also be frozen.

A great many work stations for working on histological samples are already known from the prior art. For example, work stations in the form of cutting stations, fixing stations, dehydration stations, clearing stations, infiltration stations, embedding stations or microtomes (sectioning stations) are known in many different configurations. The dehydration, clearing and infiltration can take place in different treatment stations of a single apparatus, which is designated hereinbelow as a processor.

In a cutting station, the tissue, taken from the patient for example, is cut into individual samples. The samples are for the most part placed in cassettes and transported to a fixing station. Fixing of the samples is necessary, because the oxygen supply to the cells is suppressed after the tissue has been removed from the patient, and this leads to cell death. Swelling of the cells can initially be observed, and in addition there is protein denaturation and autolysis, with subsequent bacterial digestion. In order to counteract this damage, the removed samples are fixed in the fixing station with a fixing agent, for example formalin.

Treatment in the fixing station is followed by dehydration of the sample in a dehydration station. Dehydration of the samples is necessary in order to permit the subsequent process of infiltration and of embedding.

Since the fixing agent, in particular formalin, is for the most part an aqueous medium, whereas the infiltration or embedding agent to be used, in particular paraffin, is for the most part a medium that is immiscible with water, the samples have to undergo dehydration in the dehydration station prior to the subsequent treatment of the samples. The dehydration of the samples takes place with the aid of a dehydrating agent, for example ethanol.

Before the samples are transferred to the infiltration station, they are also cleared. Clearing is necessary because the alcohol in the tissue of the sample is immiscible with paraffin. The alcohol must therefore be removed from the tissue prior to the infiltration and must be replaced by a reagent miscible with paraffin, for example xylene.

After the sample has been treated in the clearing station, it is brought to an infiltration station. In the infiltration station, an infiltration agent, which for the most part corresponds to the embedding agent to be used later, is introduced into cavities of the sample until saturation. The samples can be mechanically stabilized by the delivery of the infiltration agent.

After the sample has been treated in the infiltration station, it is worked on in the embedding station. In the embedding station, the histological sample is embedded in an embedding agent, for example paraffin or wax. In practice, the word embedding is used in two senses. On the one hand as a synonym for infiltration, which takes place in the aforementioned infiltration station, and, on the other hand, it means the same as blocking, which takes place in the embedding station.

For embedding, the samples are placed into moulds, and the mould is filled with the embedding agent. The histological sample is then cooled, such that the embedding agent can harden. To cool the histological samples, they are placed, for example, on a cooling plate of the embedding station. This results in an embedding block, in which the sample is fixed firmly in position. After the embedding agent has hardened, the sample can be sectioned, using the microtome, into individual thin sample slices, which are stained in a subsequent step and can be examined under a microscope.

To ensure that the sectioning process with the microtome can be carried out exactly, it is necessary that the embedding block remains in a hard state. In practice, a laboratory worker transports the cassettes individually from the embedding station to the microtome. Alternatively, instead of transporting the cassettes individually, it is known for the laboratory worker to instead place these from the cooling plate of the embedding station into a transport basket. The transport basket is then transported to a microtome, which is used to work on the samples present in the transport basket.

In the embodiments known from the prior art, the fixed sample is removed from the fixing container by the user and introduced into the processor. In the processor, the dehydration, clearing and infiltration of the sample take place in the corresponding abovementioned treatment stations of the processor. Thereafter, the infiltrated sample is delivered to an embedding station arranged spatially separate from the processor.

A disadvantage of the known embodiment is that the fixing containers have to be manually opened in the laboratory in order to remove the samples. Moreover, the user has to manually remove the samples from the fixing container and insert them into the processor. As a result, the user has to perform a large number of time-consuming work steps.

The object of the invention is to make available a processor and an automated system that reduces the time-consuming work steps performed by the person using the processor.

The object is achieved, for example, by a processor for working on histological samples, which has an inlet for the insertion of a fixing container with the samples located in the latter. The fixing container can be closed and can contain a large number of samples wetted by a fixing agent, for example formalin, located in the fixing container. The processor can have a single inlet.

Alternatively, the object is achieved by an automated system according to Claim 1.

Such an automated system for working on histological samples, comprises:
  a. a plurality of holding arrangements, each holding arrangement sized and shaped to hold a plurality of tissue cassettes in a single plane;
  b. a handling device disposed to transfer a holding arrangement within and between a processing area and an embedding area,
  c. the processing area comprising:
    i. a plurality of retorts,
    ii. a plurality of reagent containers;
    iii. where each retort is independently in fluid communication with a reagent container;
  d. the embedding area comprising:
    i. a dispenser for dispensing embedding material;
    II. a cooling unit; and
  e. a controller in communication with the handling device, wherein the controller is capable of receiving protocol information and directing the handling device to transport each carrier to the processing area and embedding area based on the protocol information.

The automated system can further comprise an input area sized and shaped to receive a plurality of containers, each container sized and shaped to receive a plurality of holding arrangements; wherein the handling device is further disposed to transfer holding arrangements within and between the input area and the processing area.

The automated system can further comprise an output area sized and shaped to receive a plurality of holding arrangements; wherein the handling device is further disposed to transfer the holding arrangements within and between the embedding area and the output area.

The automated system can further comprise a plurality of sensors, each operatively linked to a retort and capable of detecting the level of a reagent in the retort.

In a special embodiment of the invention the tissue cassettes remain in the holding arrangements in the processing and embedding areas.

In a special embodiment of the invention each of the holding arrangements independently carries the protocol information for tissue processing.

The automated system can further comprise a reader which reads the protocol information on the holding arrangement and communicates the protocol information to the controller.

Through the provision of an inlet for the fixing container, the user simply has to insert the fixing container into the processor. This means that the processor automatically performs at least the removal of the at least one sample or of the at least one holding arrangement from the fixing container, as a result of which the user does not need to carry out this work step. Moreover, the processor can be configured such that it automatically opens the closed fixing container in order to remove the samples from the fixing container, such that the user does not have to carry out this step either. This can be achieved by the fixing container having a slit that is closed by a flap. The flap is opened for removing the samples from the fixing container, which can be done, for example, using a handling device which is arranged in the processor and is explained below. As a result, it is possible to avoid a situation in which vapours from the fixing agent spread through the laboratory after the fixing container has been opened.

Further, the processor may be constructed to circulate the fluid within the fixing container prior to removal of the holding arrangement for processing. For example, the fixing containers could be agitated, sonicated, or could be provided with a means for circulating the fluid.

Further, the samples can be arranged in cassettes, which are releasably secured in a holding arrangement. The holding arrangement can be received by the fixing container.

The fixing container can hold one or more holding arrangements, preferably 3 or more, more preferably 5 or more. The holding arrangements can be loaded into the container simultaneously or at different times.

In one embodiment, the cassettes may be loaded into the holding arrangement by inserting the cassettes into tracks, where each subsequent cassette that is loaded pushes the preceding cassette further into the holding arrangement. The cassettes are disposed in the holding arrangement head to tail so that the base and lids are freely accessible to processing fluids and/or embedding media. While in the holding arrangement, the cassettes stay oriented relative to one another throughout processing/embedding. Ideally, cassettes which are to be processed differently are loaded into different holding arrangements. For example, one holding arrangement may contain a plurality of cassettes with breast tissues while another holding arrangement may contain a plurality of cassettes with less fatty tissues (such as muscle, skin, etc.).

In one embodiment, each holding arrangements is labelled with an identifier, including for example an RFID tag, a bar code, or another label. The identifier can carry the processing and/or embedding information for that holding arrangement. The system is designed so that a container can hold multiple holding arrangements with different identifiers that will direct the system to perform different processing and/or embedding steps. When an identifier is used, the system may also comprise a reader, such as a bar code reader or a image scanner or a receiver.

In an alternative or additional embodiment, each cassette may also be labelled with an identifier. When both the cassette and the holding arrangement are labelled, the labels may be the same or different. The labels could also be read by a reader, which could be the same or different than the reader used with the holding arrangement.

The reader(s) can be integrated with a laboratory system such as the CEREBRO platform (Leica Biosystems, Germany), which would not only track the holding arrangement (and cassettes held therein) but could also provide the processing instructions to the instrument for each holding arrangement.

In one embodiment, the holding arrangement and/or cassette may include an identifier that signals the automated system to process that holding arrangement out of turn (i.e. before previously loaded holding arrangements) to allow STAT processing of tissue samples.

In another alternate or additional embodiment, the holding arrangements and/or cassettes may also contain a means for tracking the amount of time the holding arrangement has been in contact with the fixation fluid (including formalin, formalin like or non-formalin fixatives) in the container.

In one embodiment of the invention, the samples can be worked on in a plurality of treatment stations, which are arranged in the processor, and in an embedding station arranged downstream from the treatment stations. The treatment stations include, within the meaning of the inventions, all stations in which the samples are treated after removal from the fixing container and prior to insertion into the embedding station. In particular, the treatment station can be the dehydration station, the clearing station or the infiltration station. Each of the treatment stations can have a reagent container, which is filled with a reagent and into which the samples are introduced.

Especially in the processing area, the treatment stations can be all stations in which the samples are treated after withdrawal from the fixing container and prior to insertion into the embedding station.

In an alternative embodiment, the sample can be worked on especially in a single treatment station and an embedding station arranged downstream from the treatment station. The treatment station has a single sample-receiving container, which is fluidically connected to at least one reagent container and/or is arranged spatially separate from the latter. All the treatment processes subsequent to the fixing process and prior to the embedding process can take place in the sample-receiving container.

The sample-receiving container can be connected at least to a dehydration agent container, a clearing agent container and/or an infiltration agent container. To treat the samples located in the sample-receiving container, the reagents are delivered in succession particularly only in this container. In this embodiment, the sample does not have to be transported to the different reagent containers, as a result of which a simple and compact structure of the processor is achieved.

In a particular embodiment, an embedding station can be integrated in the processor. This dispenses with a further work step for the user, since the latter no longer has to transport the infiltrated samples from the processor to the embedding station. Moreover, compared to embodiments in which the processor and the embedding station are apparatuses arranged spatially separate from each other, the structure of the processor is more compact, which is advantageous in view of the shortage of space in the laboratory. The processor can have a housing, which encloses both the embedding station and also the at least one treatment station of the processor.

After the fixing container has been inserted into the processor, it is located directly in an interior of the processor. In the latter, the fixing container can be opened in order to remove the samples. Moreover, the processor can have a suction arrangement, by means of which vapours from the fixing agent can be suctioned. As a result, a spread of vapours from the fixing agent can be easily suppressed in the laboratory.

The inlet can have a pull-out inlet drawer for the insertion of at least one fixing container. The provision of the inlet drawer affords the advantage that a plurality of fixing containers can be inserted simultaneously into the processor, which likewise makes thing easier for the user. The fixing containers can be placed in the inlet drawer when the latter has been pulled out. When the inlet drawer has been pushed in, the fixing containers are located in the interior of the processor.

In a particular embodiment, the processor can have a separating device. The separating device can spatially separate samples that are to be embedded from samples that are not to be embedded. The background to this is that in practice some samples, for a wide variety of reasons, for example because of an unfavourable section or because of their nature, cannot be treated, or at least cannot be completely treated, in particular embedded, by means of the processor. These samples that are not to be embedded are detected by the separating device and are separated from the remaining samples, which are to be embedded. The separation of the samples can take place before they are delivered to the embedding station. Thus, the separating device can have a sensor, in particular an optical sensor. Based on the values delivered by the sensor, it is possible to determine whether the sample is embedded or not. The provision of the separating device has the advantage that the person using the processor does not have to examine all the samples in order to ascertain whether they are to be embedded or not.

The processor can have at least two outlets, of which a first outlet is used to output samples that have been separated by the separating device and are not embedded. A second outlet is used to output samples that are embedded. This means that the samples not embedded can be easily identified by the user and removed.

In a particular embodiment, the processor can have a handling device by which the samples, or the holding arrangement with the cassettes and samples, are removed from the fixing container or delivered to the sample-receiving container or the reagent container. In particular, the same handling device can perform a step in which the samples are transported from one treatment station of the processor to another treatment station of the processor. Alternatively or in addition, the same handling device can perform a step in which samples are transported from one treatment station of the processor to the embedding station of the processor. A handling device designed in this way affords the advantage of having a simple construction and of at the same time ensuring that the transport between the treatment stations and/or between a treatment station and the embedding station takes place without influence by the user.

In one embodiment the handling device is an x/y robot. In another embodiment the handling device is an x/y/z robot. In one embodiment, the handling device is operated by a controller (such as a computer) that includes a scheduling program that allows multiple handling devices to be processed simultaneously and allows reprioritization of handling devices to allow STAT processing.

The processor can have at least one communications means for communicating with another communications means assigned to the sample. In particular, the communications means can be provided on the handling device. The other communications means, assigned to the sample, can be placed on the holding arrangement on which the samples are secured. At least one of the communications means can be a read and/or write means. The communications means can be an RFID chip. Moreover, at least one communications means can have a memory in which sample-specific and/or process-specific data are stored. In particular, the other communications means placed on the holding arrangement can contain sample-specific and/or process-specific data.

The data can, for example, be data concerning the time at which the samples were introduced into the fixing container. Alternatively or in addition, the data can concern the lengths of time for which the samples are wetted with the reagents. Of course, other data can also be stored in the memory. A control device can control the handling device and therefore the treatment of the samples, among other things based on the aforementioned data.

Thus, provision can be made that different process steps are selected via the communications means, in order for a plurality of samples to be treated in parallel in different treatment stations. It is also possible, via the communications means, to alter the sequence of the samples during treatment, for example in order to preferably treat urgent samples and/or to ensure optimized occupancy of the individual treatment stations.

The handling device can be designed to remove the holding arrangement from the inserted fixing container. The holding arrangement can have a holding frame, which carries at least one cassette, preferably a multiplicity of cassettes, wherein at least one sample is arranged in the cassette. As a result, a large number of the samples secured on the holding arrangement and therefore on the holding frame can be removed simultaneously from the fixing container by the handling device. The work involved in removing the samples from the fixing container is thus reduced or does not have to be carried out by the user.

Moreover, the processor can be designed in such a way that the at least one sample remains in the same cassette during at least one treatment step and an embedding step different from the treatment step. This dispenses with the work step known from the prior art in which the samples are removed from the cassette by the user and are placed manually into a mould for the embedding process. The treatment step in question can, for example, be the dehydration process, clearing process and/or infiltration process.

In a particular embodiment, it is possible to provide an operating element, in particular a single operating element, for operating the processor, in particular along with the embedding station. Alternatively or in addition, it is possible for a control software program, in particular a single control software program, to be provided for controlling the processor, in particular along with the embedding station. Simple operation and/or control is possible in this way. The processor can have an interface, in particular a single interface, for an electronic data connection. In this way, the processor can be connected at a defined interface to other data equipment.

It is also an object of the invention to make the removal of the samples from the fixing container and/or the working of the samples in the processor more efficient. This object is achieved by a holding arrangement which is used in the above-described processor. The holding arrangement, in particular a holding frame of the holding arrangement, carries at least one cassette, in particular a multiplicity of cassettes, in each of which at least one sample is arranged. A holding arrangement designed in this way affords the advantage that a multiplicity of samples are transported or worked on at the same time. Such a holding arrangement can also be employed independently of the specific use in the above-described processor for working on histological samples and to this extent is even the subject matter of an independent inventive concept.

It is a further object of the invention to make available a method for working on a histological sample, by means of which method the work steps to be carried out by the user are reduced. The object is achieved by a method for working on at least one histological sample using the above-described processor.

Alternatively, this object is achieved by the method specified in Claim 10.

The method for automated working on histological samples, can comprise the steps of:
a. loading a plurality of tissue cassettes containing tissue into at least a first and second carrier,
b. transporting the carrier to a processing area and simultaneously processing each tissue cassette in the carrier according to protocol information;
c. transporting the carrier from the processing area to an embedding area where a flowable embedding material is added to each tissue cassette in the carrier and solidified;
wherein steps (b) and (c) are individually performed for each carrier and wherein the steps can overlap;
wherein a controller instructs at least one handling device to transport the carrier within and between the processing area and the embedding area according to the tissue protocol information;
wherein each carrier is sized and shaped to hold a plurality of tissue cassettes and wherein the tissue cassettes remain in the carrier throughout steps (b)-(c).

Especially the tissue protocol information can be inputted into the controller by a user or by an identification tag on the carrier.

The method can comprise the further steps of transporting the carrier into a dehydration retort containing a dehydrating fluid and processing for a time sufficient to at least partially dehydrate the tissue samples and of transporting the carrier from the dehydration retort into an infiltrating retort containing a infiltrating fluid and processing for a time sufficient to at least partially infiltrate the tissue sample with infiltration fluid.

In a particular embodiment, the cassette can remain in the holding arrangement during at least one treatment step and/or embedding step and/or transport step. It is thereby ensured that a multiplicity of cassettes and therefore of samples can be treated and/or embedded and/or transported simultaneously.

The position of a cassette, particularly inside the interior of the processor, can remain unchanged during the at least one treatment step and/or embedding step. This is possible in particular with the processor configuration in which the treatment of the samples takes place only in the sample-receiving container. In particular, the holding arrangement and/or at least one cassette can be taken from the fixing container to the sample-receiving container. Thereafter, a treatment agent, such as a dehydrating agent, can be added to the sample-receiving container. Of course, the dehydrating agent can also be added before the introduction of the holding arrangement and/or the at least one cassette into the sample-receiving container. After the samples have been treated by the dehydrating agent, the latter is drained off and a new treatment agent, for example the clearing agent, is introduced into the container. The respective treatment agents are added and drained off until the samples have been worked on by all the necessary treatment agents.

In a particular embodiment, the position of the holding arrangement and/or of the cassette, in particular inside the interior of the processor, can be altered only during the transport of the cassette from the fixing container to the treatment station and/or during the transport of the holding arrangement and/or the cassette from the treatment station to the embedding station. This results in a simple method and in a processor of simple construction.

In this respect, a plurality of different cassettes and/or cassette holders can be controlled individually through the process stations either independently of one another or according to sample-specific boundary conditions. Here, provision can advantageously be made for a holder with a plurality of cassettes to overtake another holder. This happens, for example, if the samples contained therein are particularly important and have to be processed particularly quickly. Another reason could be that different samples require different processing times. A further advantage is that a blockage inside the apparatus is avoided, and a bottleneck situation need not arise.

According to an independent inventive concept, which can also be implemented separately from the particular aspects of the above-described processor or of the above-described system, provision can be made that the above-described processor and/or the above-described automated system has at least one handling device which is suitable for operating at least one treatment step and in addition for performing a transport step, in particular from a treatment station to a downstream embedding station. The advantage of such an integrated apparatus lies particularly in its compact size. In addition, the overall apparatus can be more simply constructed as a whole, because no complicated transfer unit is now needed between spatially separate apparatuses.

Independently of the particular aspects of the above-described processor or of the above-described system, an apparatus for treatment of histological samples is advantageous when characterized by the fact that the apparatus has at least one handling device suitable for operating at least one treatment step and additionally for performing a transport step, in particular from a treatment station to an embedding station. The advantage of an integrated apparatus of this kind lies particularly in its compact size. In addition, the overall apparatus can be more simply constructed as a whole, because no complicated transfer unit is now needed between spatially separate apparatuses.

According to a likewise independent inventive concept, which can also be implemented separately from the particular aspects of the above-described processor or of the above-described system, an apparatus for the treatment of histological samples can advantageously be provided with a plurality of treatment stations, in particular a fixing station and/or dehydrating station and/or embedding station, wherein a plurality of samples can be treated simultaneously by the apparatus and a control device controls the sequence of working on the samples according to process-specific boundary conditions, or a control device controls the sequence of working on a plurality of samples independently of one another. In particular, the above-described processor or the above-described system can additionally be configured in this way.

According to a likewise independent inventive concept, which can also be implemented separately from the particular aspects of the above-described processor or of the above-described system, a holding arrangement for holding cassettes for samples can advantageously be provided in which the mounted cassettes are coplanar to one another and/or in a common plane.

Alternatively or in addition, provision can be made that each individual cassette can also advantageously be inclined by a few degrees (for example 2 to 8 degrees, in particular 5 degrees) in order to ensure that, in an embedding process in which the mounted cassettes can also function as moulds, excess paraffin can drain off and air bubbles can be released and rise inside the liquid paraffin. Despite the inclination of the individual cassette, the cassettes mounted in one holding arrangement can still be located in a common plane.

In particular, provision can also be made, either alternatively or in addition, that the longitudinal extent of the cassettes is substantially parallel to the longitudinal extent of the holder.

Such a holding arrangement could be arranged, for example, in a formalin container, in which case provision can be made that the individual cassettes are inserted from above into the holding arrangement already located in formalin. In order to avoid bad odours, a lid with a slit could be provided which opens automatically (for example counter to a spring force) when a cassette is pushed in, and which closes automatically after the pushing-in is completed.

The individual cassettes can also be held with frictional engagement inside a holding arrangement. It is also possible to introduce the cassettes into the holder counter to the force of a spring, such that removal again from the holder is made easier. It is also possible, alternatively or in addition, that the individual cassettes are each held by being clamped on the holding arrangement.

It is also possible that the cassettes are pushed into rail-like receivers, of which several can be arranged parallel to each other. Here, provision can be made that, when a cassette is pushed in, the cassettes that have already been pushed in beforehand are pushed farther into the receiver.

A very particular and independent inventive concept relates to the patient-specific treatment of a plurality of cassettes. It is known that fewer than 10 cassettes are generally needed per patient. In this respect, provision can advantageously be made that a holding arrangement is configured precisely to carry such a number (batch). This is also with a view to treating the respective batch individually and/or patient-specifically. It is of course known to use holders for a plurality of cassettes. However, these holders are generally designed to hold ca. 300 cassettes. Of course, such a holder could also be fitted out with fewer than 10 cassettes, but this would result in a waste of reagents and also a waste of system resources.

According to a likewise independent inventive concept, which can also be implemented separately from the particular aspects of the above-described processor or of the above-described system, the cassette (which is mounted if appropriate in a holding arrangement and can additionally be designed as a mould) and/or the mould (if appropriate mounted in a holding arrangement) is cooled from below (preferably exclusively from below) during the embedding process, i.e. during the introduction of liquid paraffin.

Compared to cooling carried out from all sides, cooling exclusively from below has the advantage that no stress cracks occur within the paraffin.

There is additionally the possibility of exploiting the following effect: in the first stage of cooling, the lowermost layer of the paraffin is hardened. Since the sample lies directly on the bottom of the cassette or of the mould, the sample is thereby fixed. Since the upper face of the sample is in contact with the spring-loaded sieve which is not subsequently to be cut into, this spring-loaded sieve is now lifted in such a way that a gap of, for example, ca. 1 to 2 mm is obtained between the sample and the sieve. As soon as the lift is completed the rest of the paraffin can harden.

A lifting movement can take place with the aid of magnets, for example, which act on metal particles introduced into the plastic. Another possibility is to lift the sieve using levers or other mechanical means.

For such a procedure, it is particularly advantageous to use a holding arrangement in which the cassettes are coplanar to one another and/or in a common plane. Such a holding arrangement, which can be arranged vertically for example during the processing, can be easily turned through 90 degrees and placed on a cooling plate. However, it is also possible to use a holding arrangement in which the cassettes are arranged differently, for example in a stacked arrangement. In such an embodiment, a plurality of cooling fingers can be provided for example, which engage in the gaps in order to cool each of the individual cassettes from below.

The cooling can take place with the aid of a cooling liquid for example, which is arranged in a hose or in a closed membrane underneath the cassette. Cooling by air and/or cooling with the aid of at least one Peltier element is also possible.

The subject matter of the invention is shown schematically in the drawings and is described below with reference to the figures, in which identical elements or elements having an identical function are for the most part provided with the same reference signs.

Figure 1:
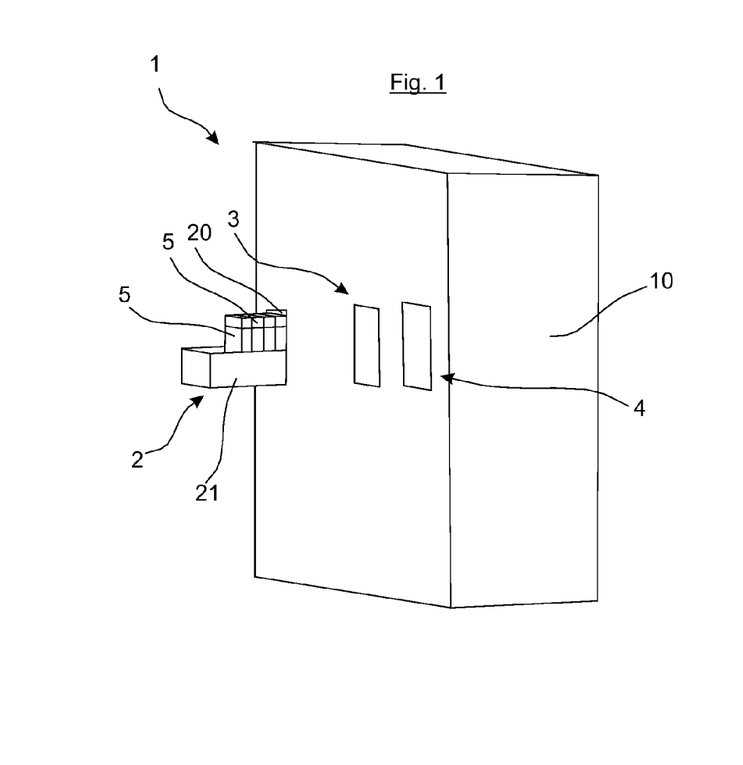
FIG. 1 shows a perspective view of the processor according to the invention with inlet drawer pulled out.

The processor 1 shown in FIG. 1 has a housing 10, an inlet 2, and a first and a second outlet 3, 4. The inlet 2 has an inlet opening 20 and a pulled-out inlet drawer 21. The drawer 21 has receivers (not shown) for receiving fixing containers 5. In the fixing containers 5, a first and a second holding frame 50, 50' of a first and a second holding arrangement are provided as shown in FIG. 2, which holding frame carries a multiplicity of cassettes 51, 51' in which at least one sample is arranged.

Figure 2:
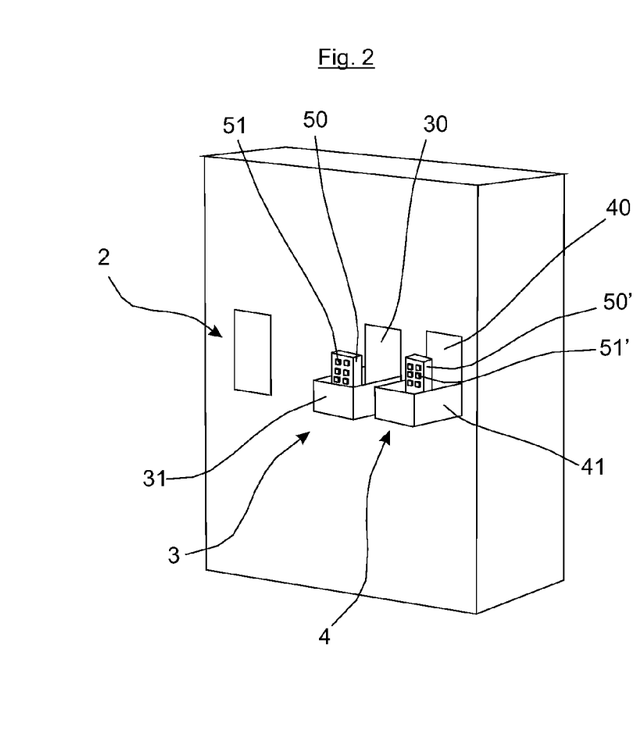
FIG. 2 shows a perspective view of the processor according to the invention with outlet drawers pulled out.

As will be seen from FIG. 2, the first outlet 3 has a first outlet opening 30 and a first outlet drawer 31, and the second outlet 4 has a second outlet opening 40 and a second outlet drawer 41. The two outlet drawers 31, 41 are pulled out and each have receivers (not shown) for receiving the holding frames 50, 50'. The first outlet drawer 31 serves to output first cassettes 51 mounted on a first holding frame 50. The first cassettes 51 contain samples that have not been embedded in the embedding station integrated in the processor 1. The second outlet drawer 41 serves to output second cassettes 51' mounted on a second holding frame 50'. The second cassettes 51' contain samples that have been embedded in the embedding station of the processor 1.

Figure 3:
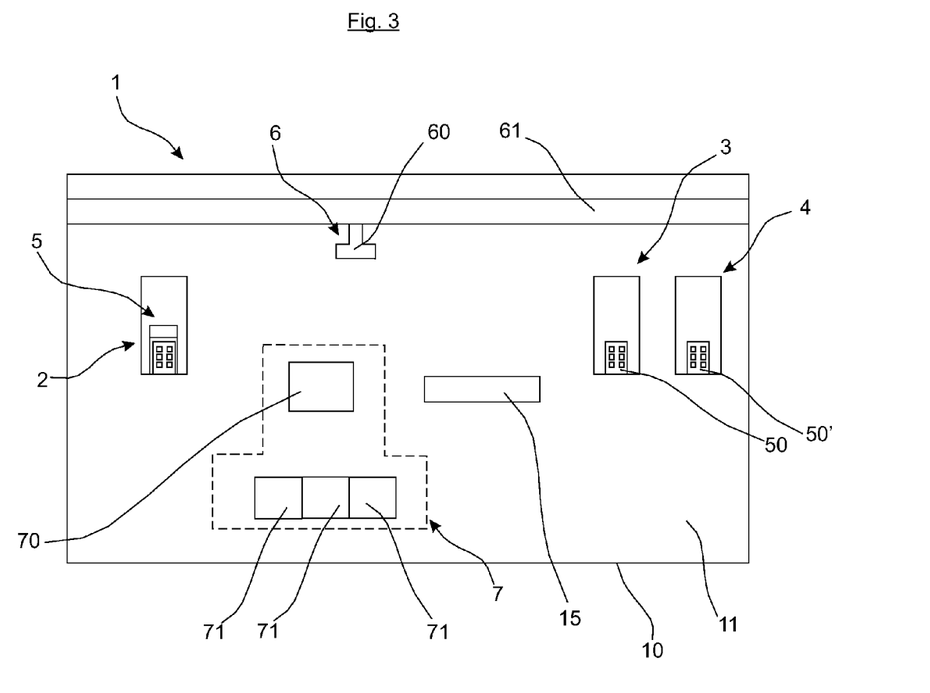
FIG. 3 shows a sectional view of the processor from the front.

FIG. 3 shows a schematic sectional view of the processor 1 from the front. In particular, FIG. 3 shows some of the components located in an interior 11 of the processor 1. The processor 1 has a handling device 6, which can move both vertically and also horizontally in the interior 11 of the processor 1 defined by the housing 10. The movement of the handling device can be guided by rails 61, with FIG. 3 showing only one rail 61, which guides the movement of the handling device 6 in the horizontal direction. The handling device 6 has a gripper 60, which can be releasably connected to the holding frame 50, 50'.

Moreover, the processor 1 has a single treatment station 7 with a sample-receiving container 70 for treatment of the samples. The sample-receiving container 70 is connected via lines (not shown) to a multiplicity of reagent containers 71 of the treatment station 7. A dehydrating agent, clearing agent or infiltration agent can be contained in the reagent container 71.

Furthermore, the processor 1 has a separating device (not shown) and an embedding station 15, which are arranged downstream from the treatment station 7. The separating device serves to determine the samples that are not to be embedded in the embedding station 15. Moreover, the separating device is arranged in a transport path of the handling device 6 between the treatment station 7 and the embedding station 15.

The mode of operation of the processor 1 is explained in the following. After the fixing containers 5 have been inserted into the inlet drawer 21 and the inlet drawer 21 has been pushed in, the gripper 60 of the handling device 6 pulls the holding frame 50, 50' out of the fixing container 5. This is possible since a lid of the fixing container 5 is provided with a slit which has a shape matching the gripper 60 and through which the gripper 60 can enter the fixing container 5 in order to remove the holding frame 50, 50' from the latter.

The handling device 6 transports the holding frame 50, 50' into the sample-receiving container 70. In the latter, the holding frame 50, 50' and therefore the samples secured on the holding frame are treated successively with several reagents provided in the reagent containers 13. Thereafter, the handling device 6 conveys the holding frames 50, 50' to the separating device, which determines whether the samples secured on the holding frame 50, 50' are or are not embedded in the embedding station 15.

The handling device 6 transports the samples to be embedded to the embedding station 15, in which the embedding of the samples takes place. After the embedding, the samples are finished and are transported by the handling device 6 to the second outlet 4. By contrast, the samples that are not to be embedded are conveyed by the handling device 6 directly from the separating device to the first outlet 3.

Figure 4:
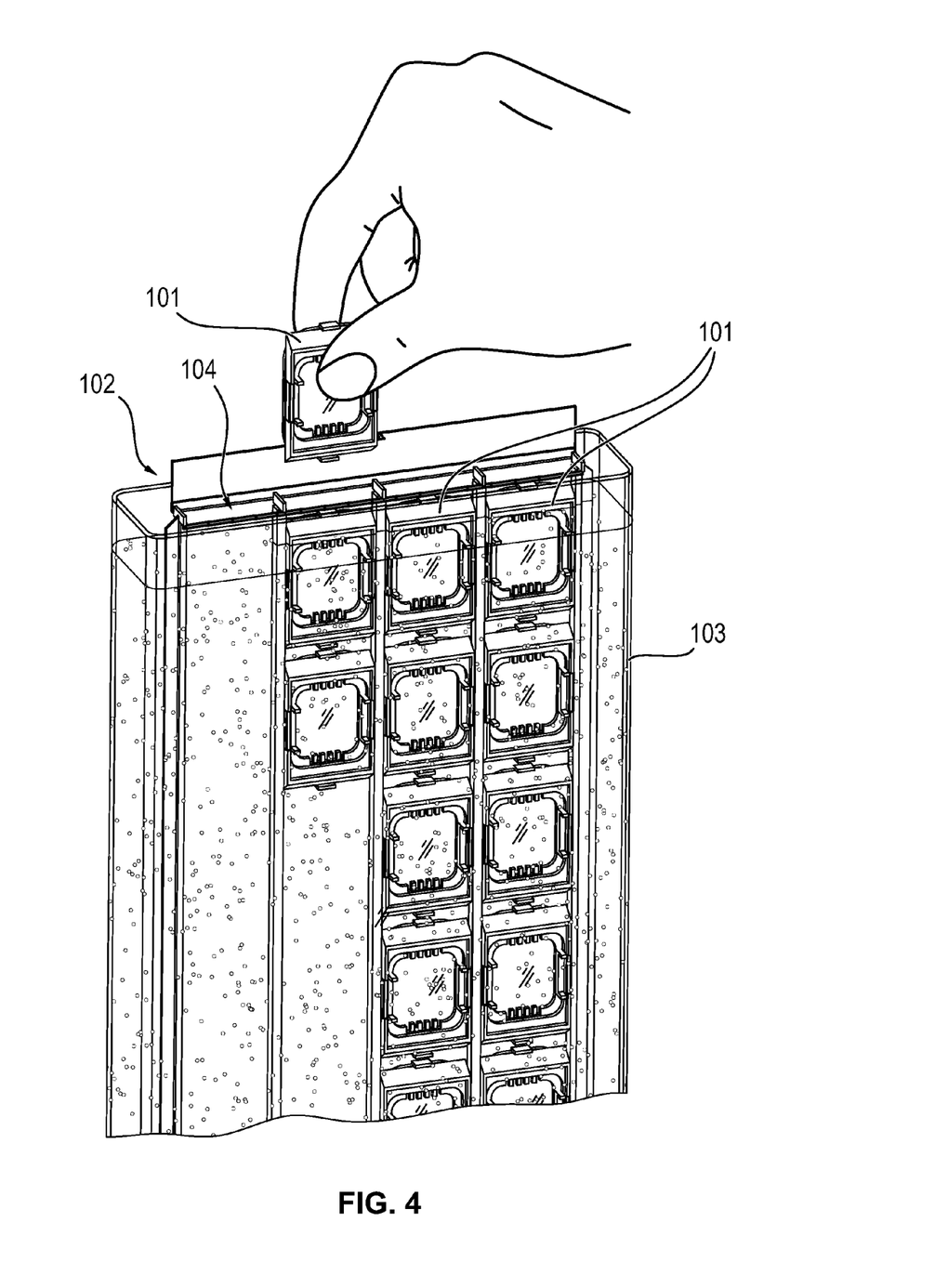
FIG. 4 shows the fitting-out of a particular holding arrangement according to an independent inventive concept.

FIG. 4 shows the fitting-out of a particular holding arrangement 102, in which the mounted cassettes 101 are coplanar to each other and in a common plane. In FIG. 4, the holding arrangement is arranged in a formalin container 103.

The cassettes are pushed into rail-like receivers 104 which are arranged parallel to each other, and of which there are four lying next to each other in this example. Provision is made here that, when a cassette 101 is pushed in, the cassettes 101 that have already been pushed in beforehand are pushed farther into the respective receiver 104. In this way, the cassettes 101 that have already been pushed in beforehand can be pushed into the formalin, without the user coming into contact with the formalin.

Figure 5:
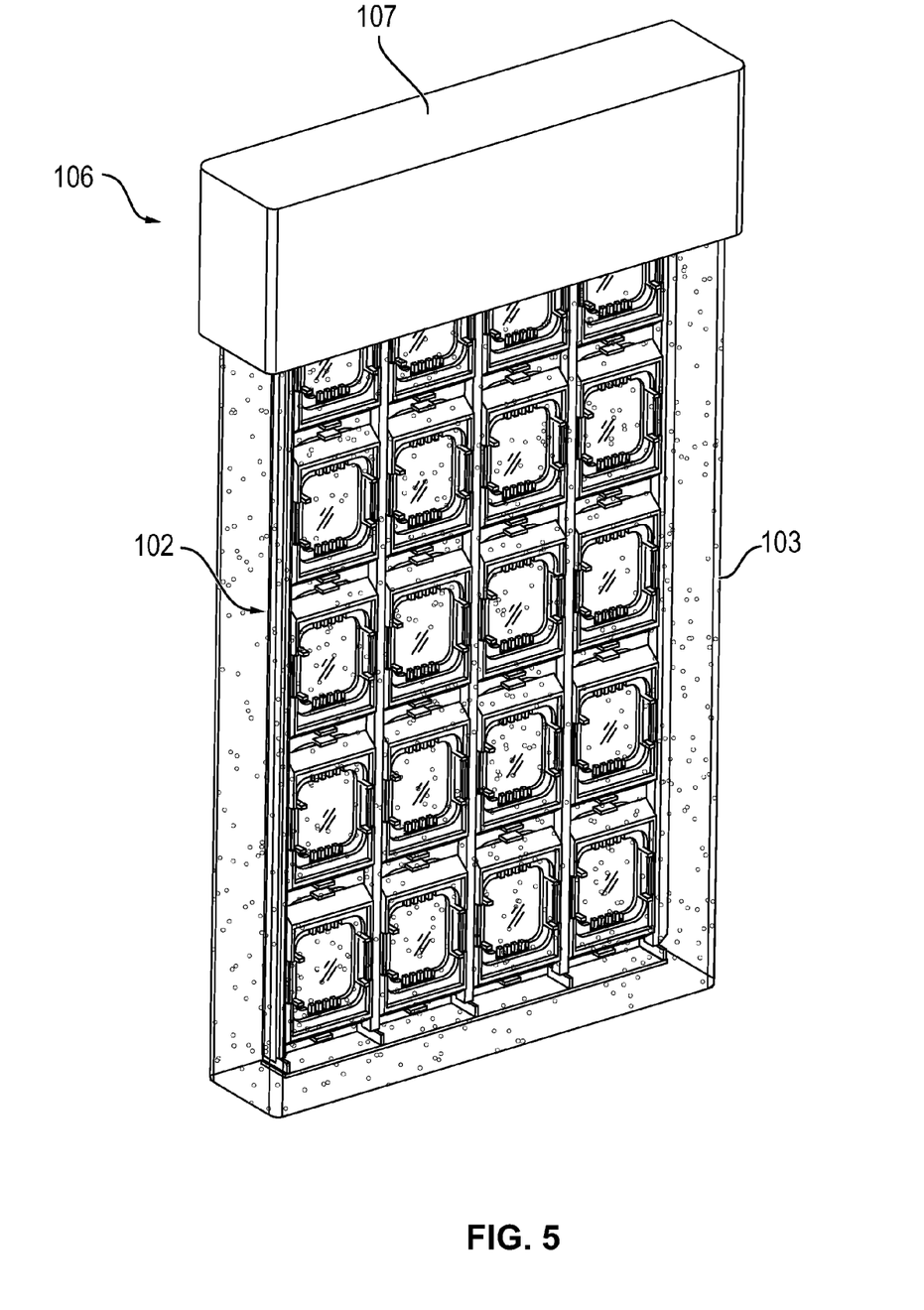
FIG. 5 shows the holding arrangement from FIG. 4 arranged in a fixing container.

FIG. 5 shows a holding arrangement 102 arranged in a fixing container 103. The fixing container has a lid 106 with a spring-loaded closure flap 107. The closure flap 107 can be designed in such a way that a handling device can press it on and remove the holding device 102. Alternatively or in addition, provision can be made that the cassettes can be introduced through the opening that the closure flap closes spring-loaded. In this way, it is possible to considerably reduce the bad odours caused by the escape of formalin vapours when fitting out the holding arrangement and when transporting the holding arrangement.

Figure 6:
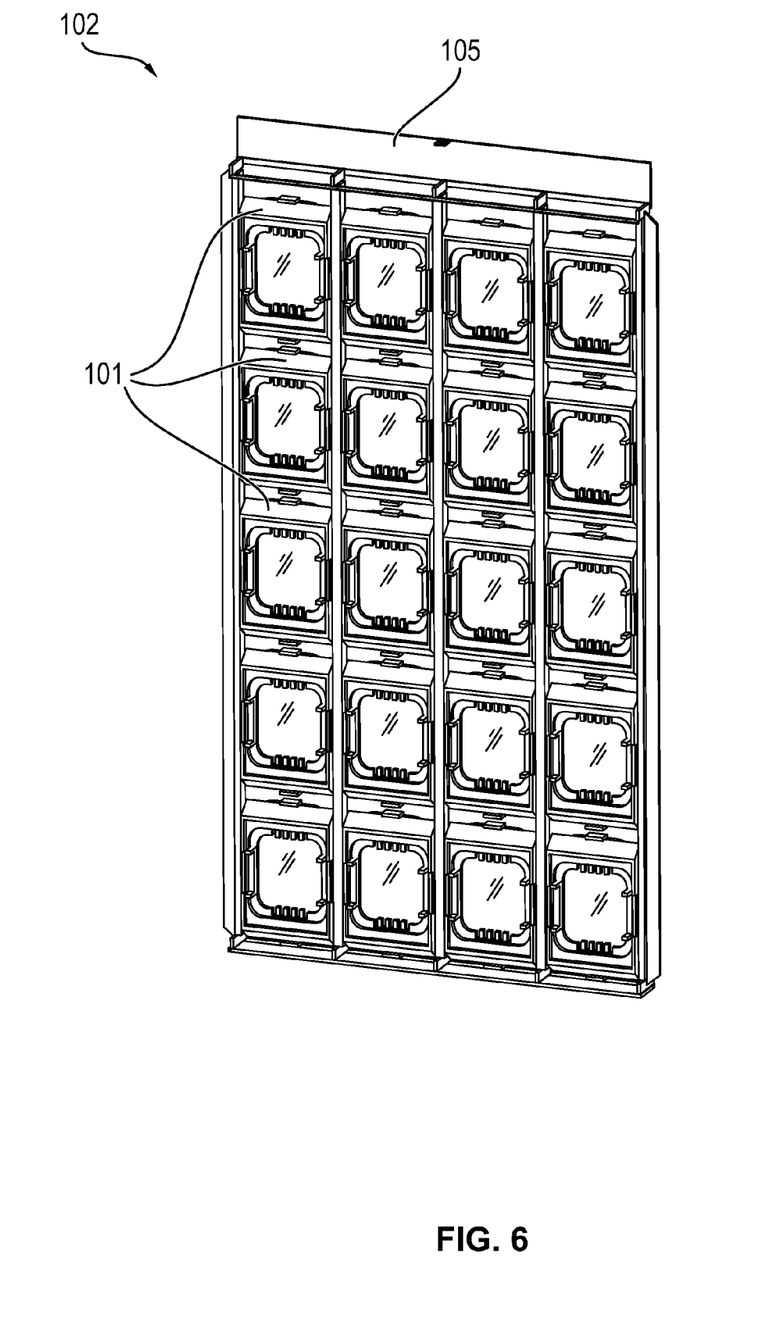
FIG. 6 shows the holding arrangement in a perspective view.

FIG. 6 shows that the holding arrangement 102 has a handling portion 105, in particular so as to be able to grip the holding arrangement 102 by robot control.

Figure 7:
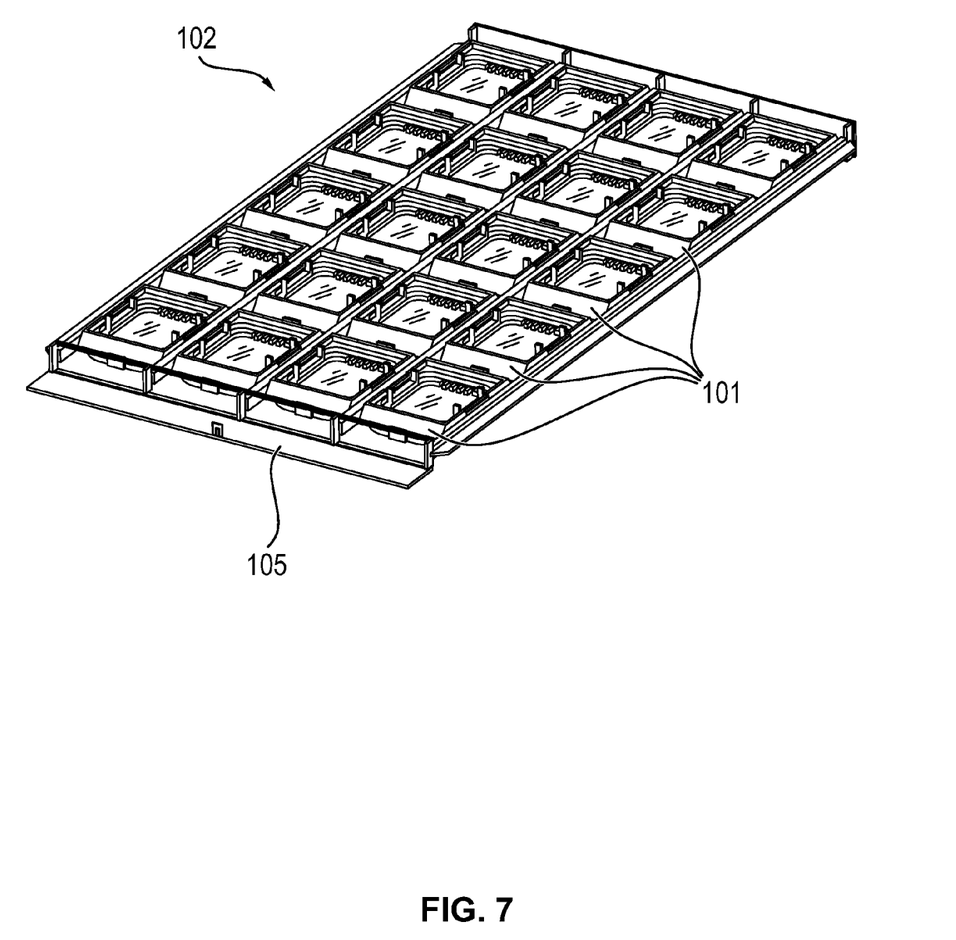
FIG. 7 shows a particular use of the holding arrangement.

FIG. 7 shows that, after a process of embedding, for example with paraffin, the holding arrangement can also be used to hold the individual blocks.

After sectioning, wax blocks can be returned to the same carrier for storage. This eliminates the need for carrier cleaning on the instrument.

Figure 8:
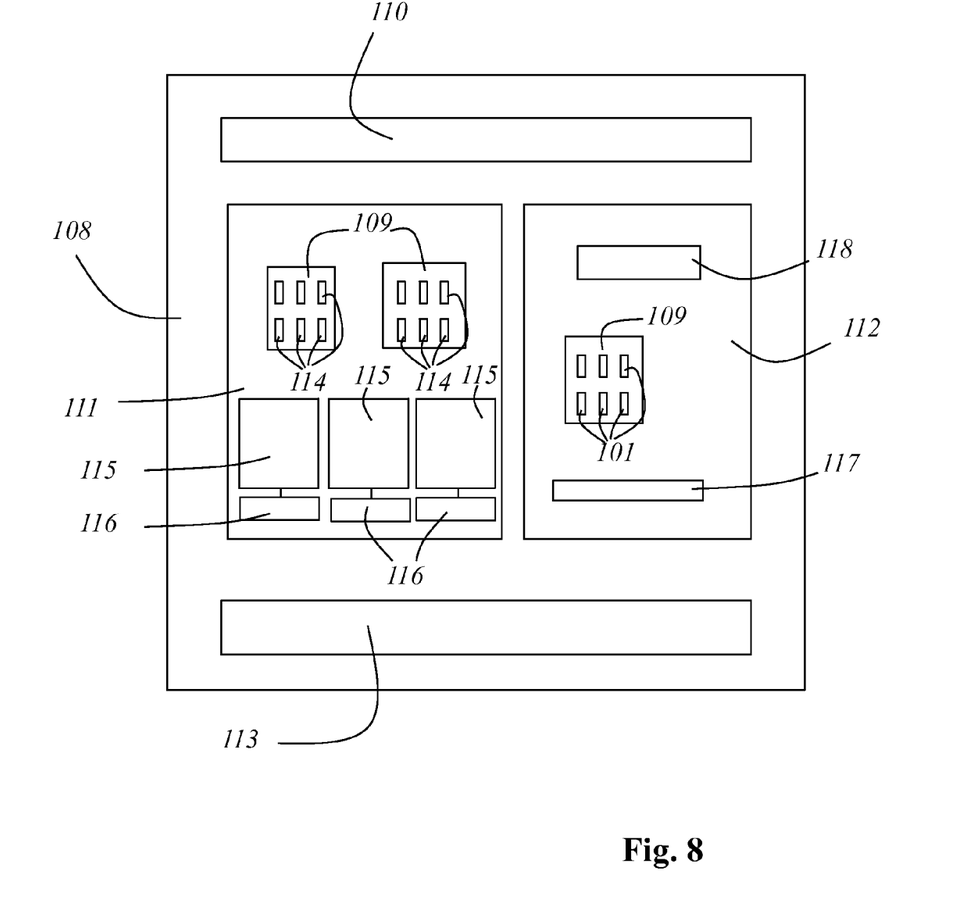
FIG. 8 shows a schematic illustrative embodiment of an automated system according to the invention.

FIG. 8 shows an automated system 108 for working on histological samples. The automated system 108 comprises a plurality of holding arrangements 109, each holding arrangement 109 sized and shaped to hold a plurality of tissue cassettes 114 in a single plane.

The automated system 108 further comprises a handling device 110 disposed to transfer a holding arrangement 109 within and between a processing area 111 and an embedding area 112.

The processing area 111 comprises a plurality of retorts 115 and a plurality of reagent containers 116, where each retort 1115 is independently in fluid communication with a reagent container 116. Further, a retort 116 may be a dehydration retort.

The embedding area 112 comprises not shown) a dispenser 118 for dispensing embedding material, a cooling unit 117.

The automated system 108 further comprises a controller 113 in communication with the handling device 110, wherein the controller 113 is capable of receiving protocol information and directing the handling device 110 to transport each carrier to the processing area 111 and embedding area 112 based on the protocol information.

LIST OF REFERENCE SIGNS

1 processor
2 inlet
3 first outlet
4 second outlet
5 fixing container
6 handling device
7 treatment station
10 housing
11 interior of the processor
15 embedding station
20 inlet opening
21 inlet drawer
30 first outlet opening
31 first outlet drawer
40 second outlet opening
41 second outlet drawer
50 first holding frame 50' second holding frame
51 first casssette
51' second cassette
60 gripper
61 rail
70 sample-receiving container
71 reagent container
101 cassette
102 holding arrangement
103 formalin container
104 receivers
105 handling portion
106 lid
107 closure flap
108 automated system
109 holding arrangement
110 handling device
111 processing area
112 embedding area
113 controller
114 tissue cassette

The invention claimed is:

1. An automated system for working on histological samples, comprising:
   a. a plurality of holding arrangements, each holding arrangement sized and shaped to hold a plurality of tissue cassettes in a single plane;
   b. a handling device disposed to transfer a holding arrangement within and between a processing area and an embedding area,
   c. the processing area comprising:
      i. a plurality of retorts,
      ii. a plurality of reagent containers;
      iii. where each retort is independently in fluid communication with a reagent container;
   d. the embedding area comprising:
      i. a dispenser for dispensing embedding material;
      ii. a cooling unit; and
   e. a controller in communication with the handling device, wherein the controller is capable of receiving protocol information and directing the handling device to transport each carrier to the processing area and embedding area based on the protocol information.

2. The automated system of claim 1, further comprising an input area sized and shaped to receive a plurality of containers, each container sized and shaped to receive a plurality of holding arrangements; wherein the handling device is further disposed to transfer holding arrangements within and between the input area and the processing area.

3. The automated system of claim 2, wherein each container is capable of holding up to 5 holding arrangements.

4. The automated system of claim 2, wherein each container is capable of holding up to 3 holding arrangements.

5. The automated system of claim 1, further comprising an output area sized and shaped to receive a plurality of holding arrangements; wherein the handling device is further disposed to transfer the holding arrangements within and between the embedding area and the output area.

6. The automated system of claim 1, further comprising a plurality of sensors, each operatively linked to a retort and capable of detecting the level of a reagent in the retort.

7. The automated system of claim 1, wherein the tissue cassettes remain in the holding arrangements in the processing and embedding areas.

8. The automated system of claim 1, wherein each holding arrangement independently carries the protocol information for tissue processing.

9. The automated system of claim 8, further comprising a reader which reads the protocol information on the holding arrangement and communicates the protocol information to the controller.

10. A method for automated processing of histological samples, comprising:
    a. loading a plurality of tissue cassettes containing tissue into at least a first and second carrier,
    b. transporting the carrier to a processing area and simultaneously processing each tissue cassette in the carrier according to protocol information;
    c. transporting the carrier from the processing area to an embedding area where a flowable embedding material is added to each tissue cassette in the carrier and solidified;
    wherein steps (b) and (c) are individually performed for each carrier and wherein the steps can overlap;
    wherein a controller instructs at least one handling device to transport the carrier within and between the processing area and the embedding area according to the tissue protocol information;
    wherein each carrier is sized and shaped to hold a plurality of tissue cassettes and wherein the tissue cassettes remain in the carrier throughout steps (b)-(c).

11. The method of claim 10, wherein the tissue protocol information is inputted into the controller by a user or by an identification tag on the carrier.

12. The method of claim 10, wherein processing comprises:
    a. transporting the carrier into a dehydration retort containing a dehydrating fluid and processing for a time sufficient to at least partially dehydrate the tissue samples;
    b. transporting the carrier from the dehydration retort into an infiltrating retort containing a infiltrating fluid and processing for a time sufficient to at least partially infiltrate the tissue sample with infiltration fluid.

13. The method of claim 10, which is conducted on an automated device comprising:
    a. a plurality of holding arrangements, each holding arrangement sized and shaped to hold a plurality of tissue cassettes in a single plane;
    b. a handling device disposed to transfer a holding arrangement within and between a processing area and an embedding area,
    c. the processing area comprising:
       i. a plurality of retorts,
       ii. a plurality of reagent containers;
       iii. where each retort is independently in fluid communication with a reagent container;
    d. the embedding area comprising:
       i. a dispenser for dispensing embedding material;
       ii. a cooling unit; and
    e. a controller in communication with the handling device, wherein the controller is capable of receiving protocol information and directing the handling device to transport each carrier to the processing area and embedding area based on the protocol information.

* * * * *